United States Patent [19]

Eidenschink et al.

[11] Patent Number: 4,478,740
[45] Date of Patent: Oct. 23, 1984

[54] BENZONITRILES

[75] Inventors: Rudolf Eidenschink, Dieburg; Jürgen Eichler, Breuberg; Georg Weber, Erzhausen, all of Fed. Rep. of Germany

[73] Assignee: Merck Patent Gesellschaft mit beschränkter Haftung, Darmstadt, Fed. Rep. of Germany

[21] Appl. No.: 467,990

[22] Filed: Feb. 18, 1983

[30] Foreign Application Priority Data

Feb. 18, 1982 [DE] Fed. Rep. of Germany ....... 3205766

[51] Int. Cl.³ .................... C09K 3/34; C07C 121/60
[52] U.S. Cl. .................. 252/299.62; 252/299.63; 252/299.66; 260/465 R; 260/465 F; 350/350 R
[58] Field of Search .................... 260/465 R, 465 F; 252/299.62, 299.63, 299.66

[56] References Cited

U.S. PATENT DOCUMENTS 4,130,502 12/1978 Eidenschink et al. ............ 252/299
4,349,452 9/1982 Osman et al. .................. 252/299.61
4,368,135 1/1983 Osman ......................... 252/299.63
4,415,470 11/1983 Eidenschink et al. ........... 252/299.63

FOREIGN PATENT DOCUMENTS 2027027 2/1980 United Kingdom .

Primary Examiner—Dolph H. Torrence
Attorney, Agent, or Firm—Millen & White

[57] ABSTRACT

New benzonitriles of formula I

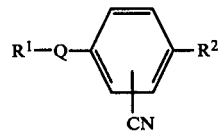

wherein $R^1$ and $R^2$ are each alkyl groups of 1–8 C atoms, and one of these radicals can also be alkoxy of 1–8 C atoms, and Q is one or two radicals selected from 1,4-phenylene, 1,4-cyclohexylene and/or 1,4-bicyclo[2.2.2]octylene, are very useful for preparing liquid crystallene dielectrics and electrooptical display elements based thereon.

14 Claims, No Drawings

BENZONITRILES

BACKGROUND OF THE INVENTION

For electrooptical display elements whose operation is based on the phenomenon of dynamic scattering, deformation of oriented phases (DOP effect) or absorption of light by orientatable dichroic dyestuffs, liquid crystal dielectrics are required which have a significant negative dielectric anisotropy (DCA) and in which the dielectric constant (DC) parallel to the molecular axis is smaller than the DC perpendicular to the molecular axis. The more negative the DCA of the liquid crystal dielectric is, the smaller is the threshold voltage for operation of such display elements. A further basic requirement of such dielectrics is a broad temperature range for the nematic phase, including room temperature.

Of the customary liquid crystal base materials of such dielectrics, there is none with a markedly negative DCA. In order to prepare liquid crystal dielectrics with a marked negative DCA using these materials, it is necessary to add liquid crystal compounds having a very highly negative DCA. These compounds are usually insufficiently soluble in the liquid crystal base materials, are unstable as esters, and/or cause an undesirable shift in the nematic temperature range. If need be, the solubility problems can be solved by using several compounds having a negative DCA, but this is accomplished at the expense of an increase in the viscosity of the nematic phase and the resulting undesirable increase in the switching times of the display element.

SUMMARY OF THE INVENTION

It is an object of this invention to provide new stable liquid crystal base materials of low viscosity for dielectrics with a significantly negative DCA.

Upon further study of the specification and appended claims, further objects and advantages of this invention will become apparent to those skilled in the art.

These objects have been achieved by providing the new benzonitriles of Formula I

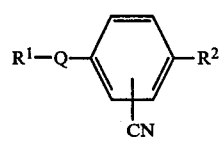

I wherein $R^1$ and $R^2$ are each independently alkyl of 1–8 C atoms, or one of these radicals can also be alkoxy of 1–8 C atoms and Q is one or two radicals selected from 1,4-phenylene, 1,4-cyclohexylene and/or 1,4-bicyclo[2.2.2]octylene.

These substances can, like similar compounds, for example those known from German Offenlegungsschrift No. 2,933,563, whose disclosure is incorporated by reference herein, be used as components of liquid crystal dielectrics, in particular for displays based on the principle of dynamic scattering.

The invention thus relates to the benzonitriles of Formula I, processes for their preparation and their use as components of liquid crystal dielectrics. The invention furthermore relates to liquid crystal dielectrics containing at least one benzonitrile of Formula I, and electrooptical display elements based on a liquid crystal cell containing such a liquid crystal dielectric.

DETAILED DISCUSSION

It has been found that the benzonitriles of Formula I are outstandingly suitable as components of liquid crystal dielectrics. In particular, stable liquid crystal phases with a highly negative dielectric anisotropy (DCA) can be prepared using these compounds. The arrangement, which is unusual for liquid crystal base materials, of the nitrile groups in the lateral position relative to the longitudinal molecular axis evidently results in the markedly negative dielectric anisotropy. The latter is a prerequisite for the use of these compounds in electrooptical displays which are based on the phenomenon of dynamic scattering, deformation of oriented phases or light absorption by orientatable dichroic dyestuffs.

The compounds of Formula I thus have an exceptionally wide field of use. Depending on the selection of the substituents, these compounds can be used as base materials from which liquid crystal dielectrics are predominantly composed, or the compounds of Formula I can also be added to liquid crystal materials from other classes of compounds, in order, for example, to reduce the mean DCA of such a dielectric.

The compounds of Formula I are colorless in the pure state, and form liquid crystal mesophases in the temperature range which can readily be utilized for electrooptical applications. As benzonitriles, they are stable.

The benzonitriles of Formula I of this invention include, in particular, the preferred phenylbenzonitriles of Formula Ia, cyclohexyl-benzonitriles of Formula Ib, cyclohexyl-phenyl-benzonitriles of Formula Ic and bicyclo [2.2.2]octylene-phenyl-benzonitriles of Formula Id

| | |
|---|---|
| $R^1$—Phe—Phe(CN)—$R^2$ | Ia |
| $R^1$—Cy—Phe(CN)—$R^2$ | Ib |
| $R^1$Cy—Phe—Phe(CN)—$R^2$ | Ic |
| $R^1$—Bi—Phe—Phe(CN)—$R^2$ | Id | wherein, in each case, Phe is 1,4-phenylene, Cy is 1,4-cyclohexylene, Bi is bicyclo[2.2.2]octylene and Phe(CN) is 1,4-phenylene substituted by nitrilo in the 2-, 3-, 5- or 6-position.

The Formula I also includes the preferred benzonitrile derivatives of Formulae Ie to Il.

| | |
|---|---|
| $R^1$—Bi—Phe(CN)—$R^2$ | Ie |
| $R^1$—Cy—Cy—Phe(CN)—$R^2$ | If |
| $R^1$—Phe—Phe—Phe(CN)—$R^2$ | Ig |
| $R^1$—Phe—Cy—Phe(CN)—$R^2$ | Ih |
| $R^1$—Bi—Cy—Phe(CN)—$R^2$ | Ii |
| $R^1$—Phe—Bi—Phe(CN)—$R^2$ | Ik |
| $R^1$—Bi—Bi—Phe(CN)—$R^2$ | Il | wherein $R^1$, $R^2$, Bi, Cy, Phe and Phe(CN) are as defined above. Also included are the derivatives of the formula $R^1$—Cy—Bi—Phe(CN)—$R^2$.

In the compounds of Formula I and Ia to Il which contain cyclohexylene radicals, those stereoisomers wherein the two 1,4-substituents are in each case in the transposition relative to one another are preferred.

In the compounds of Formula I, the alkyl and alkoxy radicals $R^1$ and $R^2$ can in principle be straight-chain or branched.

They are preferably straight-chained and accordingly preferably are methyl, ethyl, n-propyl, n-butyl, n-pentyl, n-hexyl, n-heptyl, n-octyl, methoxy, ethoxy, n-propoxy, n-butoxy, n-pentyloxy, n-hexyloxy, n-heptyloxy or n-octyloxy.

Compounds of Formula I with straight-chain end group substituents $R^1$ and $R^2$ as a rule have higher clear points than the analogous compounds with branched end group substituents $R^1$ and $R^2$. Because of this, the compounds of the present invention are usually provided with at most one branched end group substituent $R^1$ or $R^2$.

Compounds of Formula I with a branched end group substituent $R^1$ or $R^2$ may occasionally be of importance because of their better solubility in the customary liquid crystal base materials, but, in particular, as chiral doping substances, if they possess optical activity as a result of the chain branching. Branched end group substituents $R^1$ or $R^2$ as a rule contain no more than one chain branching. Preferred branched radicals $R^1$ and $R^2$ are isopropyl, 2-methylpropyl, 2-methylbutyl, 3-methylbutyl, 2-methylpentyl, 3-methylpentyl, 2-ethylhexyl, 1-methylhexyl, 1-methylheptyl, 2-ethyl-pentyl, isopropoxy, 2-methylpropoxy, 2-methylbutoxy, 3-methylbutoxy, 2-methylpentyloxy, 3-methylpentyloxy, 2-ethylhexyloxy, 1-methylhexyloxy and 1-methylheptyloxy. The groups $R^1$ and $R^2$ in each case contain 1 to 8, preferably 3 to 5, C atoms. Alkyl groups are preferred to the alkoxy groups.

The compounds of Formula I can be prepared by methods which are known per se for similar compounds, such as those described in the literature (for example in the standard works such as Houben-Weyl, Methoden der organischen Chemie (Methods of Organic Chemistry), Georg Thieme Verlag, Stuttgart, whose disclosure is incorporated by reference herein), and in particular under reaction conditions which are known and suitable for these reactions. It is also possible to use variants which are known per se and are not mentioned here in more detail.

If desired, the starting substances can also be formed in situ, in a manner such that they are not isolated from the reaction mixture but are immediately reacted further to give the compounds of Formula I.

The compounds of Formula I wherein $R^2$ is an alkoxy group are preferably prepared by converting, as the starting material, for example, a known compound of the formula $R^1$—Q—Phe—$R^2$ into a compound of the formula $R^1$—Q—Phe(X)—$R^2$ wherein X is a halogen atom, Cl, Br or iodine or a nitro group $NO_2$, by conventional electrophilic substitution, conventionally converting the substituent X, if this is $-NO_2$, into a diazonium salt group by reduction and diazotization, and finally conventionally converting the halogen or diazonium salt group into the nitrile group by reaction with a metal cyanide. Preferred suitable metal cyanides are heavy metal cyanides, preferably $Cu_2(CN)_2$. The reaction is carried out in water or, better, in the presence of an inert solvent, such as dimethylformamide, N-methylpyrrolidone or dimethylsulfoxide, at temperatures of about 0 to 150 degrees centigrade.

Alternatively, the compounds of Formula I can be obtained by dehydrating an amide of the formula $R^1$—Q—Phe(CO—NH)—$R^2$ or an oxime of the formula $R^1$—Q—Phe(CH=NOH)—$R^2$.

Examples of suitable agents which split off water include inorganic acid chlorides, such as $SOCl_2$, $PCl_3$, $PCl_5$, $SO_2Cl_2$ and $COCl_2$, and furthermore $P_2O_5$, $P_2S_5$, $AlCl_3$ as a double-compound with NaCl, aromatic sulfonic acids and sulfonic acid halides. The reaction is carried out in the presence or absence of an inert solvent, for example an aromatic hydrocarbon, such as benzene, toluene or xylene, preferably at temperatures of about 50 to 150 degrees centigrade.

A process for the preparation of the compounds of Formula I accordingly comprises reacting a compound of Formula II

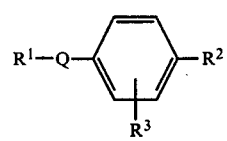

wherein $R^3$ is Cl, Br, I or a diazonium salt group and $R^1$ and $R^2$ are as defined above, with a metal cyanide, or dehydrating a compound of Formula III

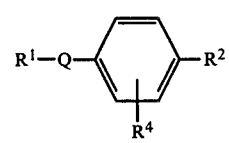

wherein $R^4$ is —$CONH_2$ or —CH=NOH and $R^1$ and $R^2$ are as defined above.

Most of the starting materials of Formulae II and III are new. However, they can be routinely prepared by methods which are known per se. The preparation of the compounds of Formula II has already been illustrated above.

The compounds of Formula III can be obtained, for example, from the corresponding benzoic acids, benzoyl chlorides, benzoic acid esters or benzaldehydes by reaction with ammonia or hydroxylamine. The benzaldehydes required can be conventionally prepared, for example, by controlled oxidation of the corresponding benzyl alcohol or by formylation of the corresponding phenol and subsequent etherification.

The dielectrics of this invention comprise 2 to 15, preferably 3 to 12, components, at least one of which is a benzonitrile of Formula I. The other constituents are preferably selected from nematic or nematogenic substances, in particular the known substances from the classes of azoxybenzenes, benzylideneanilines, biphenyls, terphenyls, phenyl or cyclohexyl benzoates, phenyl or cyclohexyl cyclohexanecarboxylates, phenylcyclohexanes, cyclohexylbiphenyls, cyclohexylcyclohexanes, cyclohexylnaphthalenes, 1,4-bis-cyclohexylbenzenes, 4,4'-bis-cyclohexylbiphenyls, phenyl- or cyclohexyl-pyrimidines, phenyl- or cyclohexyldioxanes, optionally halogenated stilbenes, benzyl phenyl ethers, tolanes and substituted cinnamic acids.

The most important compounds which can be used as constituents of such liquid crystal dielectrics can be described by Formula IV

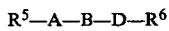

$$R^5-A-B-D-R^6 \quad \text{IV}$$

wherein A and D are each a carbocyclic or heterocyclic ring system selected from 1,4-disubstituted benzene and cyclohexane rings, 4,4'-disubstituted biphenyl, phenylcyclohexane and cyclohexylcyclohexane systems, 2,5-disubstituted pyrimidine and 1,3-dioxane rings, 2,6-disubstituted naphthalene, di- and tetra-hydronaphthalene, quinazoline and tetrahydroquinazoline; B is —CH=CH—, —CH=CY—, —C≡C—, —CO—O—, —CO—S—, —CH=N—, —N(O)=N—, —CH=N(O)—, —CH₂—CH₂—, —CH₂—O—, —CH₂—S—, —COO—Ph—COO— or a C—C single bond; Y is halogen, preferably chlorine, or —CN; and $R^5$ and $R^6$ are alkyl, alkoxy, alkanoyloxy or alkoxycarbonyloxy of up to 18, preferably up to 8, carbon atoms, or one of these radicals is —CN, —NC, —NO₂—, —CF₃, F, Cl or Br.

In most of these compounds, $R^5$ and $R^6$ differ from one another, one of these radicals usually being an alkyl or alkoxy group. Other variants of the envisaged substituents can also be used. Many such substances and mixtures thereof are commercially available.

The dielectrics of this invention contain 0.1 to about 60% by weight of the compounds of Formula I. As a rule, they contain 5 to 55%, preferably 10 to 50%, by weight of one or more compounds of Formula I.

The dielectrics according to this invention are prepared in a manner which is customary per se. As a rule, the desired amount of the component used in the smaller amount is dissolved in the component which makes up the main constituent, preferably at elevated temperature. If a temperature above the clear point of the main constituent is chosen, it is particularly easy to observe the completeness of the solution operation.

The liquid crystal dielectrics according to this invention can be modified by suitable additives such that they can be used in all the types of liquid crystal display elements which have hitherto been disclosed.

Such additives are familiar to the expert and are described in detail in the relevant literature. For example, it is possible to add conductive salts, preferably ethyl-dimethyl-dodecyl-ammonium 4-hexyloxybenzoate, tetrabutylammonium tetraphenylboranate or complex salts of crown ethers (compare, for example, I. Haller et al., Mol. Cryst. Liq. Cryst. Volume 24, pages 249-258 (1973)) to improve the conductivity, dichroic dyestuffs, or substances for modifying the dielectric anisotropy, the viscosity and/or the orientation of the nematic phases. Such substances are described in, for example, German Offenlegungsschriften Nos. 2,209,127, 2,240,864, 2,321,632, 2,338,281, 2,450,088, 2,637,430, 2,853,728 and 2,902,177.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever. In the following examples, all temperatures are set forth uncorrected in degrees Celsius; unless otherwise indicated, all parts and percentages are by weight.

In the examples, m.p. is the melting point and c.p. is the clear point of a liquid crystal substance in degrees centigrade.

EXAMPLE 1

A mixture of 325 g of 2-bromo-2-(trans-4-propylcyclohexyl)-ethoxybenzene [oil; obtainable by bromination of 4-trans-(4-propylcyclohexyl)-ethoxybenzene], 160 g of Cu₂(CN)₂ and 1 liter of N-methylpyrrolidone is stirred at 175° for 4 hours, cooled to 20°, left to stand overnight and poured into a solution of 1 kg of NaCN in 20 liters of water. After the mixture has been stirred at 95° for one hour, it is extracted with toluene. Customary working up gives 2-ethoxy-5-(trans-4-propyl-cyclohexyl)-benzonitrile of m.p. 32°.

Examples 2 to 55

The following compounds can be obtained analogously to Example 1, by bromination of the corresponding benzene derivatives and subsequent reaction with Cu₂(CN)₂:

2. 4'-Propyl-4-methoxy-5-cyano-biphenyl.
3. 4'-Butyl-4-ethoxy-5-cyano-biphenyl.
4. 4'-Hexyl-4-ethoxy-5-cyano-biphenyl.
5. 4'-Octyl-4-propoxy-5-cyano-biphenyl.
6. 4'-Propyl-4-propoxy-5-cyano-biphenyl.
7. 4'-Butyl-4-propoxy-5-cyano-biphenyl.
8. 4'-Pentyl-4-butoxy-5-cyano-biphenyl, m.p. 35°, c.p. −40°.
9. 4'-Pentyl-4-butoxy-5-cyano-biphenyl.
10. 4'-Pentyl-4-hexyloxy-5-cyano-biphenyl, m.p. 41°, c.p. 28°.
11. 4'-Hexyl-4-hexyloxy-5-cyano-biphenyl.
12. 2-Propoxy-5-(trans-4-methyl-cyclohexyl)-benzonitrile.
13. 2-Propoxy-5-(trans-4-butyl-cyclohexyl)-benzonitrile.
14. 2-Propoxy-5-(trans-4-hexyl-cyclohexyl)-benzonitrile.
15. 2-Butoxy-5-(trans-4-propyl-cyclohexyl)-benzonitrile.
16. 2-Butoxy-5-(trans-4-butyl-cyclohexyl)-benzonitrile.
17. 2-Butoxy-5-(trans-4-hexyl-cyclohexyl)-benzonitrile.
18. 2-Pentyloxy-5-(trans-4-propyl-cyclohexyl)-benzonitrile.
19. 2-Pentyloxy-5-(trans-4-pentyl-cyclohexyl)-benzonitrile.
20. 2-Hexyloxy-5-(trans-4-butyl-cyclohexyl)-benzonitrile.
21. 2-Hexyloxy-5-(trans-4-hexyl-cyclohexyl)-benzonitrile.
22. 2-Octyloxy-5-(trans-4-propyl-cyclohexyl)-benzonitrile.
23. 4'-(trans-4-Methyl-cyclohexyl)-4-butoxy-5-cyano-biphenyl.
24. 4'-(trans-4-Propyl-cyclohexyl)-4-propoxy-5-cyano-biphenyl.
25. 4'-(trans-4-Pentyl-cyclohexyl)-4-hexyloxy-5-cyano-biphenyl, m.p. 53°, c.p. 119°.
26. 4'-(trans-4-(2-Methylbutyl)-cyclohexyl)-4-propoxy-5-cyano-biphenyl.
27. 4'-(trans--cyano-biphenyl.

30. 4'-(trans-4-Propyl-cyclohexyl-4-hexyloxy-5-cyano-biphenyl.
31. 4'-(trans-4-Pentyl-cyclohexyl-4-heptyloxy-5-cyano-biphenyl.
32. 4'-(trans-4-Propyl-cyclohexyl)-4-ethyl-5-cyano-biphenyl.
33. 4'-(trans-4-Butyl-cyclohexyl)-4-propyl-5-cyano-biphenyl.
34. 4'-(4-Propyl-bicyclo[2.2.2]octyl)-4-propoxy-5-cyano-biphenyl.
35. 4'-(4-Propyl-bicyclo[2.2.2]octyl)-4-butoxy-5-cyano-biphenyl.
36. 4'-(4-Butyl-bicyclo[2.2.2]octyl)-4-(2-methylbutoxy)-5-cyano-biphenyl.
37. 4'-(4-Pentyl-bicyclo[2.2.2]octyl)-4-hexyloxy-5-cyano-biphenyl.
38. 2-Propoxy-5-(4-ethyl-bicyclo[2.2.2]octyl)-benzonitrile.
39. 2-Butoxy-5-(4-ethyl-bicyclo[2.2.2]octyl)-benzonitrile.
40. 2-Pentyloxy-5-(4-butyl-bicyclo[2.2.2]octyl)-benzonitrile.
41. 2-Hexyloxy-5-(4-butyl-bicyclo[2.2.2]octyl)-benzonitrile.
42. 2-Octyloxy-5-(4-propyl-bicyclo[2.2.2]octyl)-benzonitrile
43. 2-Butoxy-5-(4-(4'-propyl-bicyclohexyl))-benzonitrile of the formula propyl-Cy-Cy-Phe(CN)-O-butyl.
44. 2-Butoxy-5-(4-(4'-pentyl-bicyclohexyl))-benzonitrile.
45. 2-Propoxy-5-(4-(4'-propyl-biphenyl))-benzonitrile.
46. 2-Hexyloxy-5-(4-(4'-butyl-biphenyl))-benzonitrile of the formula butyl-Phe-Phe-Phe(CN)-O-hexyl.
47. 2-Propoxy-5-(trans-4-(4-propyl-phenyl)-cyclohexyl)-benzonitrile of the formula propyl-Phe-Cy-Phe(CN)-O-propyl.
48. 2-Butoxy-5-(trans-4-(4-butyl-phenyl)-cyclohexyl)-benzonitrile.
49. 2-Propoxy-5-(trans-4-(4-propyl-bicyclo[2.2.2]octyl)-cyclohexyl)-benzonitrile of the formula propyl-Bi-Cy-Phe(CN)-O-propyl.
50. 2-Pentyloxy-5-trans-4-(4-butyl-bicyclo[2.2.2]octyl)-cyclohexyl)-benzonitrile.
51. 2-Pentyl-5-(trans-4-(4-pentyl-bicyclo[2.2.2]octyl)-cyclohexyl)-benzonitrile of the formula pentyl-Bi-Cy-Phe(CN)-pentyl.
52. 2-Butoxy-5-(4-(4-propyl-phenyl)-bicyclo[2.2.2]octyl)-benzonitrile of the formula propyl-Phe-Bi-Phe(CN)-O-butyl.
53. 2-Pentyloxy-5-(4-(4-butyl-phenyl)-bicyclo[2.2.2]octyl-benzonitrile.
54. 2-Butoxy-5-(4'-propyl-4,4'-bis-(bicyclo[2.2.2]octyl))-benzonitrile of the formula propyl-Bi-Bi-Phe(CN)-O-butyl.
55. 2-Hexyloxy-5-(4'-pentyl-4,4'-bis-(bicyclo[2.2.2]octyl))-benzonitrile.

EXAMPLE 56

26.1 g of 2-ethoxy-5-(trans-4-propylcyclohexyl)-aniline [obtainable, for example, by nitration of trans-1-(4-ethoxyphenyl)-4-propylcyclohexane and subsequent hydrogenation of the resulting 2-ethoxy-5-(trans-4-propyl-cyclohexyl)-nitrobenzene] is dissolved in a mixture of 25 g of concentrated hydrochloric acid and 75 ml of water and is diazotized at 3 to 6° with a solution of 8 g of NaNO₂ in 15 ml of water.

The diazonium salt solution is added to a Cu₂(CN)₂ solution (prepared by warming 25 g of copper sulfate with 28 g of KCN in 100 ml of water), warmed to 60° to 70°, in the course of 15 minutes. The mixture is warmed to 100° for a further 20 minutes and cooled to give, after customary working up, 2-ethoxy-5-(trans-4-propylcyclohexyl)-benzonitrile of m.p. 32°.

The benzonitrile derivatives listed in Examples 2 to 55 can be obtained analogously from the corresponding aromatics.

EXAMPLE 57

18 g of SOCl₂ is added, at 80°, to a suspension of 28.9 g of 2-ethoxy-5-(trans-4-propyl-cyclohexyl)-benzamide [obtainable, for example, by reaction of trans-1-(4-hydroxyphenyl)-4-propyl-cyclohexane with chloroform/KOH to give 2-ethoxy-5-(trans-4-propylcyclohexyl)-benzaldehyde, oxidation to the acid, reaction with SOCl₂ to give the chloride and reaction with NH₃] in 100 ml of toluene. After the mixture has been stirred at 80° for 6 hours, cooled and poured into water, 2-ethoxy-5-(trans-4-propyl-cyclohexyl)-benzonitrile of m.p. 32° is obtained.

The benzonitrile derivatives listed in Examples 2 to 55 can also be obtained analogously.

EXAMPLE 58

A mixture of 28.9 g of 2-ethoxy-5-(trans-4-propyl-cyclohexyl)-benzaldoxime (obtainable from the aldehyde and hydroxylamine) and 40 ml of acetic anhydride is heated until the exothermic reaction starts, and is then boiled for 20 minutes and poured into water to give 2-ethoxy-5-(trans-4-propyl-cyclohexyl)-benzonitrile of m.p. 32°.

The benzonitrile derivatives listed in Examples 2 to 55 can also be obtained analogously.

The following compounds can also be obtained by dehydration of the corresponding oximes:
59. 4,4'-Dibutyl-6-cyano-biphenyl.
60. 4,4'-Dihexyl-6-cyano-biphenyl.
61. 4'-(trans-4-Pentyl-cyclohexyl)-4-hexyloxy-6-cyano-biphenyl.
62. 2-Pentyloxy-6-(4-butyl-bicyclo[2.2.2]octyl)-benzonitrile.
63. 2-Pentyloxy-6-(4-(4'-propyl-biphenyl))-benzonitrile.
64. 2-Butoxy-6-(trans-4-(4-propyl-phenyl)-cyclohexyl)-benzonitrile.

The following examples are examples of dielectrics according to this invention containing at least one compound of Formula I.

EXAMPLE A

A mixture of 5% of trans-1-p-ethoxyphenyl-4-propyl-cyclohexane, 8% of 1-p-(trans-4-pentylcyclohexyl)-phenylpentane-1,3-dione, 13% of 4-butoxy-3-cyano-4,-pentylbiphenyl, 30% of 4-ethyl-2'-fluoro-4'-(trans-4-pentylcyclohexyl)-biphenyl, 23% of p-pentylphenyl p-methoxybenzoate, 8% of 4-ethyl-4'-(trans-4-propyl-cyclohexyl)-biphenyl, 7% of 4-ethyl-4'-(trans-4-pentyl-cyclohexyl)-biphenyl and 6% of 4-(trans-4-pentylcyclohexyl)-4'-(trans-4-propylcyclohexyl)-biphenyl has the following properties: m.p. −14°, c.p. 83°.

EXAMPLE B

A mixture of 15% of trans-1-(p-ethoxyphenyl)-4-propylcyclohexane, 11% of trans-1-(p-butoxyphenyl)-4-propylcyclohexane, 15% of 2-ethoxy-5-(trans-4-propylcyclohexyl)-benzonitrile, 26% of 4-ethyl-2,2'-difluoro-4'-(trans-4-pentylcyclohexyl)-biphenyl, 14% of 4-ethyl-4'-(trans-4-propylcyclohexyl)-biphenyl, 12% of 4-ethyl-4'-(trans-4-pentylcyclohexyl)-biphenyl and 7% of 4-(trans-4-pentylcyclohexyl)-4'-(trans-4-propylcyclohexyl)-biphenyl has the following properties: m.p. −12°, c.p. 88°.

EXAMPLE C

A mixture of 23% of trans-1-p-ethylphenyl-4-propylcyclohexane, 15% of 3-cyano-4-ethoxy-4'-propylbiphenyl, 26% of 4-ethyl-2'-fluoro-4'-(trans-4-pentylcyclohexyl)-biphenyl, 16% of 4-ethyl-4'-(trans-4-propylcyclohexyl)-biphenyl, 10% of 4-ethyl-4'-(trans-4-pentylcyclohexyl)-biphenyl and 10% of 4-(trans-4-pentylcyclohexyl)-4'-trans-(4-propylcyclohexyl)-biphenyl has the following properties: m.p. −13°, c.p. 67°.

The preceding examples can be repeated with similar success by substituting the generically or specifically described reactants and/or operating conditions of this invention for those used in the preceding examples. From the foregoing description, one skilled in the art can easily ascertain the essential characteristics of this invention, and without departing from the spirit and scope thereof, can make various changes and modifications of the invention to adapt it to various usages and conditions.

What is claimed is:

1. A benzonitrile of the formula

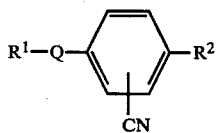

wherein
R$^1$ and R$^2$ are each independently alkyl of 1–8 C atoms, or one is C$_{1-8}$-alkyl and the other is alkoxy of 1–8 C atoms; and
Q is one or two groups selected from 1.4-phenylene, 1,4-cyclohexylene and/or 1,4-bicyclo[2.2.2]-octylene.

2. A compound of claim 1 of the formula

R$^1$—Phe—Phe(CN)—R$^2$

R$^1$—Cy—Phe(CN)—R$^2$

R$^1$Cy—Phe—Phe(CN)—R$^2$

R$^1$—Bi—Phe—Phe(CN)—R$^2$, wherein Phe is 1,4-phenylene, Cy is 1,4-cyclohexylene, Bi is 1,4-bicyclo[2.2.2]octylene and Phe(CN) is 1,4-phenylene substituted by nitrilo in the 2-, 3-, 5- or 6-position.

3. A compound of claim 1 of the formula

R$^1$—Bi—Phe(CN)—R$^2$

R$^1$—Cy—Cy—Phe(CN)—R$^2$

R$^1$—Phe—Phe—Phe(CN)—R$^2$

R$^1$—Phe—Cy—Phe(CN)—R$^2$

R$^1$—Bi—Cy—Phe(CN)—R$^2$

R$^1$—Phe—Bi—Phe(CN)—R$^2$

R$^1$—Bi—Bi—Phe(CN)—R$^2$ wherein Phe is 1,4-phenylene, Cy is 1,4-cyclohexylene, Bi is 1,4-bicyclo[2.2.2]octylene and Phe(CN) is 1,4-phenylene substituted by nitrilo in the 2-, 3-, 5- or 6-position.

4. A compound of claim 1 wherein R$_1$ and R$_2$ are straight chained.

5. A compound of claim 1 wherein only one of R$_1$ or R$_2$ is branched and it has only one chain branching.

6. A compound of claim 1 wherein R$_1$ and R$_2$ each have 3–5 C atoms.

7. A compound of claim 4 wherein R$_1$ and R$_2$ are alkyl.

8. A compound of claim 2 of the formula

R$^1$—Phe—Phe(CN)—R$^2$ or

R$^1$—Bi—Phe—Phe(CN)—R$^2$.

9. A compound of claim 3 of the formula

R$^1$—Bi—Phe(CN)—R$^2$

R$^1$—Phe—Phe—Phe(CN)—R$^2$

R$^1$—Bi—Cy—Phe(CN)—R$^2$

R$^1$—Phe—Bi—Phe(CN)—R$^2$

R$^1$—Bi—Bi—Phe(CN)—R$^2$.

10. A compound of claim 1 of the formula

R$^1$—Cy—Bi—Phe(CN)—R$^2$

R$^1$—Bi—Phe—Phe(CN)—R$^2$

R$^1$—Bi—Phe(CN)—R$^2$

R$^1$—Bi—Cy—Phe(CN)—R$^2$

R$^1$—Phe—Bi—Phe(CN)—R$^2$

R$^1$—Bi—Bi—Phe(CN)—R$^2$.

11. A liquid crystal dielectric useful in electrooptical display elements comprising at least two liquid crystal compounds, wherein at least one compound is a benzonitrile of claim 1.

12. A liquid crystal dielectric of claim 11 comprising 3–12 liquid crystal compounds.

13. A liquid crystal dielectric of claim 11 wherein the amount of said benzonitrile is 0.1–60 wt. %.

14. In an electrooptical display element based on a liquid crystal cell comprising a liquid crystal dielectric, the improvement wherein the dielectric is that of claim 11.

* * * * *